US012667243B2

(12) United States Patent
Tofach et al.

(10) Patent No.: US 12,667,243 B2
(45) Date of Patent: Jun. 30, 2026

(54) ARTICULATING ENDOSCOPE WITH WORKING CHANNEL

(71) Applicant: Covidien LP, Mansfield, MA (US)

(72) Inventors: Shai Tofach, Louisville, CO (US);
Chenghao Bi, Boulder, CO (US);
Derek S. Tata, Longmont, CO (US)

(73) Assignee: Covidien LP, Mansfield, MA (US)

( * ) Notice: Subject to any disclaimer, the term of this patent is extended or adjusted under 35 U.S.C. 154(b) by 287 days.

(21) Appl. No.: 18/612,289

(22) Filed: Mar. 21, 2024

(65) Prior Publication Data

US 2024/0358234 A1     Oct. 31, 2024

Related U.S. Application Data

(60) Provisional application No. 63/498,681, filed on Apr. 27, 2023.

(51) Int. Cl.
*A61B 1/00*          (2006.01)
*A61B 1/005*         (2006.01)
(Continued)

(52) U.S. Cl.
CPC ........ *A61B 1/0011* (2013.01); *A61B 1/00097* (2022.02); *A61B 1/00114* (2013.01);
(Continued)

(58) Field of Classification Search
CPC .............. A61B 1/0011; A61B 1/00097; A61B 1/00124; A61B 1/0057; A61B 1/0018; A61B 1/05; F16B 13/146
See application file for complete search history.

(56) References Cited

U.S. PATENT DOCUMENTS 4,407,273 A * 10/1983 Ouchi .................... A61B 17/29
                                                        600/107
5,156,590 A    10/1992 Vilmar
                    (Continued)

FOREIGN PATENT DOCUMENTS

CN        205458557       8/2016
EP         2433553 A1     3/2012
                    (Continued)

OTHER PUBLICATIONS

International Search Report for International Application No. PCT/IB2024/053953 mailed Jun. 26, 2024 (13 pages).
(Continued)

*Primary Examiner* — John P Leubecker
*Assistant Examiner* — Peter Nguyen

(57)          ABSTRACT

The present technology relates to articulating endoscopes and methods for manufacturing articulating endoscopes. An example endoscope includes an outer jacket extending a length of the endoscope; an outer wall, interior to the outer jacket, of an extrusion extending at least 80% of the length of the endoscope and ending at a bendable region of the endoscope; an inner wall, interior to the outer wall, extending at least 90% of a length of the endoscope and through the bendable region, the inner wall defining a working channel through the endoscope; a plurality of fins extending from the inner wall to the outer wall and defining a plurality of auxiliary channels between the inner wall and the outer wall; a first pull wire extending through a first auxiliary channel of the plurality of auxiliary channels; and a second pull wire extending through a second auxiliary channel of the plurality of auxiliary channels.

15 Claims, 7 Drawing Sheets

(51) Int. Cl.

| | |
|---|---|
| *A61B 1/018* | (2006.01) |
| *A61B 1/05* | (2006.01) |

(52) U.S. Cl.
CPC ........ *A61B 1/00124* (2013.01); *A61B 1/0057* (2013.01); *A61B 1/018* (2013.01); *A61B 1/05* (2013.01)

(56) References Cited

U.S. PATENT DOCUMENTS

| | | | | |
|---|---|---|---|---|
| 5,372,587 | A * | 12/1994 | Hammerslag | A61M 25/0144 604/95.04 |
| 5,397,304 | A * | 3/1995 | Truckai | A61M 25/0147 604/528 |
| 6,458,076 | B1 * | 10/2002 | Pruitt | A61B 1/0051 600/128 |
| 7,762,949 | B2 * | 7/2010 | Nakao | A61B 1/00073 600/125 |
| 8,194,122 | B2 | 6/2012 | Amling et al. | |
| 8,652,033 | B2 | 2/2014 | Berci et al. | |
| 8,715,172 | B1 | 5/2014 | Girgis | |
| 8,746,239 | B2 | 6/2014 | Yoshida | |
| 8,827,899 | B2 | 9/2014 | Farr et al. | |
| 8,982,199 | B2 | 3/2015 | Amling et al. | |
| 9,123,155 | B2 | 9/2015 | Cunningham et al. | |
| 9,282,993 | B1 * | 3/2016 | Cohen | A61B 17/3421 |
| 9,498,112 | B1 | 11/2016 | Stewart et al. | |
| 9,538,908 | B2 | 1/2017 | Allyn et al. | |
| 9,687,141 | B2 | 6/2017 | McGrath | |
| 9,820,641 | B2 | 11/2017 | McGrath | |
| 10,010,379 | B1 | 7/2018 | Gibby et al. | |
| 10,149,957 | B2 | 12/2018 | Runnels | |
| 11,006,975 | B1 * | 5/2021 | Cohen | A61B 17/3421 |
| 11,931,001 | B2 * | 3/2024 | Do | A61B 1/0011 |
| 2005/0131279 | A1 * | 6/2005 | Boulais | A61B 1/0016 600/141 |
| 2006/0178658 | A1 | 8/2006 | Smith | |
| 2006/0247494 | A1 * | 11/2006 | Nakagawa | A61B 1/018 600/104 |
| 2007/0197896 | A1 | 8/2007 | Moll et al. | |
| 2007/0236514 | A1 | 10/2007 | Agusanto et al. | |
| 2008/0177146 | A1 | 7/2008 | Chen | |
| 2008/0177148 | A1 | 7/2008 | Chen et al. | |
| 2008/0312507 | A1 | 12/2008 | Kim | |
| 2011/0130632 | A1 | 6/2011 | McGrail et al. | |
| 2011/0137127 | A1 | 6/2011 | Schwartz | |
| 2011/0245609 | A1 | 10/2011 | Laser | |
| 2011/0264089 | A1 * | 10/2011 | Zirkle | A61B 5/6852 606/41 |
| 2013/0057667 | A1 | 3/2013 | McGrath | |
| 2013/0197555 | A1 * | 8/2013 | Schaer | A61N 7/022 606/170 |
| 2013/0267838 | A1 | 10/2013 | Fronk et al. | |
| 2014/0031700 | A1 | 1/2014 | Ferrantelli | |
| 2014/0160261 | A1 | 6/2014 | Miller et al. | |
| 2014/0275760 | A1 | 9/2014 | Lee et al. | |
| 2014/0378763 | A1 | 12/2014 | Atarot | |
| 2016/0066950 | A1 | 3/2016 | Kucklick | |
| 2016/0199009 | A1 | 7/2016 | Gilboa | |
| 2016/0279365 | A1 | 9/2016 | Esnouf | |
| 2017/0055809 | A1 | 3/2017 | Omoto | |
| 2017/0209071 | A1 | 7/2017 | Zhao et al. | |
| 2017/0258313 | A1 | 9/2017 | McGrath | |

| | | | | |
|---|---|---|---|---|
| 2018/0193102 | A1 | 7/2018 | Inoue | |
| 2018/0292199 | A1 | 10/2018 | Tojo | |
| 2018/0296281 | A1 | 10/2018 | Yeung et al. | |
| 2018/0324352 | A1 | 11/2018 | Furuhata | |
| 2019/0133430 | A1 | 5/2019 | Inglis et al. | |
| 2020/0029793 | A1 | 1/2020 | McGrath | |
| 2020/0195903 | A1 | 6/2020 | Komp et al. | |
| 2020/0254204 | A1 | 8/2020 | Moffat et al. | |
| 2020/0275824 | A1 | 9/2020 | Tata | |
| 2020/0367742 | A1 | 11/2020 | McGrath | |
| 2020/0383561 | A1 | 12/2020 | McGrath | |
| 2021/0052140 | A1 | 2/2021 | Tata | |
| 2021/0121155 | A1 | 4/2021 | Maguire | |
| 2021/0127949 | A1 | 5/2021 | Tata | |
| 2021/0128033 | A1 | 5/2021 | Tata | |
| 2021/0137350 | A1 | 5/2021 | Inglis | |
| 2021/0257856 | A1 | 8/2021 | Ng | |
| 2021/0259536 | A1 | 8/2021 | Inglis | |
| 2021/0275008 | A1 | 9/2021 | McGrath | |
| 2021/0318382 | A1 | 10/2021 | McGrath | |
| 2022/0110504 | A1 | 4/2022 | Inglis | |
| 2022/0225859 | A1 | 7/2022 | Phillips | |
| 2022/0257092 | A1 | 8/2022 | Ng | |
| 2022/0354380 | A1 | 11/2022 | Tata | |
| 2023/0029630 | A1 | 2/2023 | Ng | |
| 2024/0358234 | A1 * | 10/2024 | Tofach | A61B 1/00097 |
| 2025/0075724 | A1 * | 3/2025 | Spirk | F16B 13/146 |
| 2025/0161641 | A1 * | 5/2025 | Gad | A61M 25/0147 |

FOREIGN PATENT DOCUMENTS

| | | | |
|---|---|---|---|
| JP | 2014210085 | A | 11/2014 |
| WO | 02/41766 | A1 | 5/2002 |
| WO | 2016/138495 | A1 | 9/2016 |
| WO | 2020/005890 | A1 | 1/2020 |
| WO | 2022/133248 | A1 | 6/2022 |
| WO | 2022/266500 | A1 | 12/2022 |

OTHER PUBLICATIONS

Ambu_aScope_3_Large_Brochure_4963605 (Oct. 2017).

McGrath Mac—Video Laryngoscope Operator's Manual Instructions for Use—Aircraft Medical Ltd (2017) www.aircraftmedical.com—23 pages.

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS ONE | https://doi.org/10.1371/journal.pone.0186691 (Nov. 3, 2017).

* cited by examiner

500

558
570
559C
572
A
559A
D6
559B
W2

500

558
570
559C
572
545
A
559A
564
559B

500

558
580
545
572
564

700

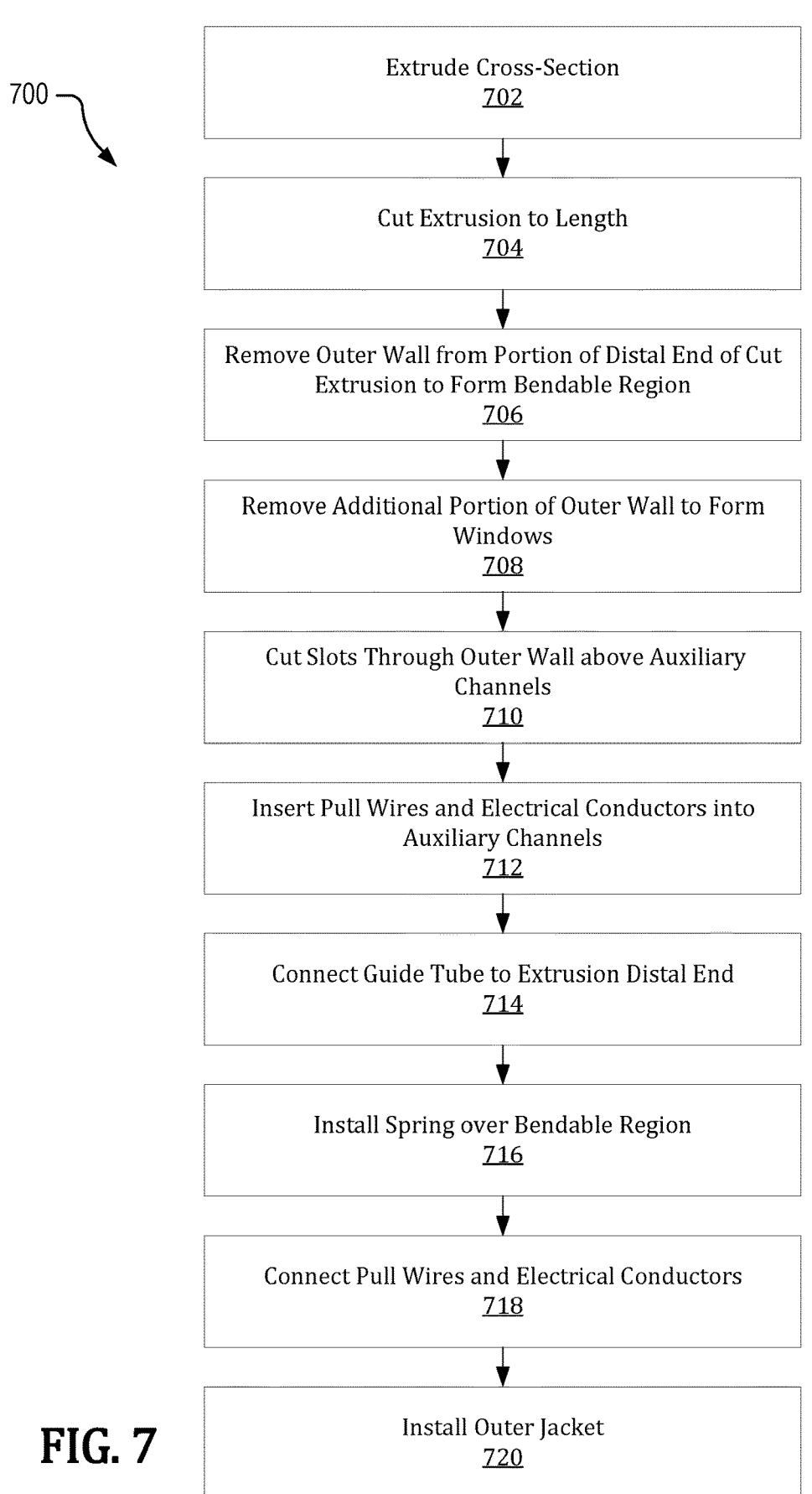

Extrude Cross-Section
702

Cut Extrusion to Length
704

Remove Outer Wall from Portion of Distal End of Cut Extrusion to Form Bendable Region
706

Remove Additional Portion of Outer Wall to Form Windows
708

Cut Slots Through Outer Wall above Auxiliary Channels
710

Insert Pull Wires and Electrical Conductors into Auxiliary Channels
712

Connect Guide Tube to Extrusion Distal End
714

Install Spring over Bendable Region
716

Connect Pull Wires and Electrical Conductors
718

Install Outer Jacket
720

FIG. 7

ARTICULATING ENDOSCOPE WITH WORKING CHANNEL

CROSS-REFERENCE TO RELATED APPLICATION

The present application claims the benefit of U.S. Provisional Patent Application Ser. No. 63/498,681, filed on Apr. 27, 2023, the entire content of which is incorporated herein by reference.

BACKGROUND

Laryngoscopes are commonly used to perform intubations on patients who require breathing assistance. During an intubation, the laryngoscope may be used to manipulate the anatomy of the larynx and associated structures of a patient's airway, in order to obtain a view sufficient for insertion of a breathing tube (e.g., an endotracheal tube) into the trachea. In some situations, the anatomy of the patient, or injury or other health condition of the patient, may prevent a clinician from obtaining a clear view of the larynx. In situations where intubation of a patient may be difficult, an endoscope may be used to aid visualization of the larynx and insertion of the breathing tube. An endoscope is a narrow, flexible tube that typically includes a light and camera at an insertable end of the tube and is inserted into the body for visualizing anatomical structures of a patient. The use of an endoscope may assist the clinician in performing an intubation.

It is with respect to this general technical environment that aspects of the present technology disclosed herein have been contemplated. Furthermore, although a general environment is discussed, it should be understood that the examples described herein should not be limited to the general environment identified herein.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Additional aspects, features, and/or advantages of examples will be set forth in part in the description which follows and, in part, will be apparent from the description, or may be learned by practice of the disclosure.

In an aspect, the technology relates to a method for manufacturing an endoscope. The method includes extruding a cross-section to form an extrusion. The extrusion includes an inner wall defining a first lumen; an outer wall defining a second lumen between the inner wall and the outer wall; and a plurality of fins extending from the inner wall to the outer wall and defining a plurality of auxiliary channels in the second lumen. The method further includes removing the outer wall from a portion of a distal end of the extrusion to form a bendable region; cutting slots in the outer wall above at least two of the auxiliary channels; inserting a pull wire through one of the slots and into one of the auxiliary channels; and installing an outer jacket covering the extrusion including the bendable region.

In an example, the method further includes cutting the extrusion to a length of the endoscope. In another example, the method further includes installing a spring over the auxiliary channels of the bendable region. In yet another example, the method includes inserting electrical conductors through the slots and into the auxiliary channels. In still another example, the method further includes routing a distal end of the pull wire around posts protruding from a mounting ring; and thermally reflowing the posts to secure the pull wire to the mounting ring. In still yet another example, the plurality fins include at least 4 fins.

In another aspect, the technology relates to an endoscope including an outer jacket extending a length of the endoscope; an outer wall, interior to the outer jacket, of an extrusion extending at least 80% of the length of the endoscope and ending at a bendable region of the endoscope; an inner wall, interior to the outer wall, extending at least 90% of a length of the endoscope and through the bendable region, the inner wall defining a working channel through the endoscope; a plurality of fins extending from the inner wall to the outer wall and defining a plurality of auxiliary channels between the inner wall and the outer wall; a first pull wire extending through a first auxiliary channel of the plurality of auxiliary channels; and a second pull wire extending through a second auxiliary channel of the plurality of auxiliary channels.

In an example, the first auxiliary channel is positioned opposite the working channel from the second auxiliary channel. In another example, the endoscope further includes a third pull wire extending through a third auxiliary channel of the plurality of auxiliary channels; and a fourth pull wire extending through a fourth auxiliary channel of the plurality of auxiliary channels, wherein the fourth auxiliary channel is positioned opposite the working channel from the third auxiliary channel. In yet another example, an access window is cut in the outer wall, above the first auxiliary channel, adjacent and proximal to the bendable region. In still another example, the first pull wire is positioned within a first separate lumen and the second pull wire is positioned with a second separate lumen. In a further example, the endoscope also includes a camera positioned at a distal end of the endoscope; and an electrical conductor electrically coupled to the camera and extending through a third auxiliary channel of the plurality of auxiliary channels.

In another example, the endoscope includes a spring wrapped around the bendable region and positioned interior to the outer jacket. In still another example, the plurality of fins include at least 6 fins. In yet another example, the endoscope further includes a guide tube, at a distal end of the endoscope, supporting one or more sensors.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

FIG. 7 depicts an example method for fabricating a steerable endoscope.

DETAILED DESCRIPTION

Figure 1:
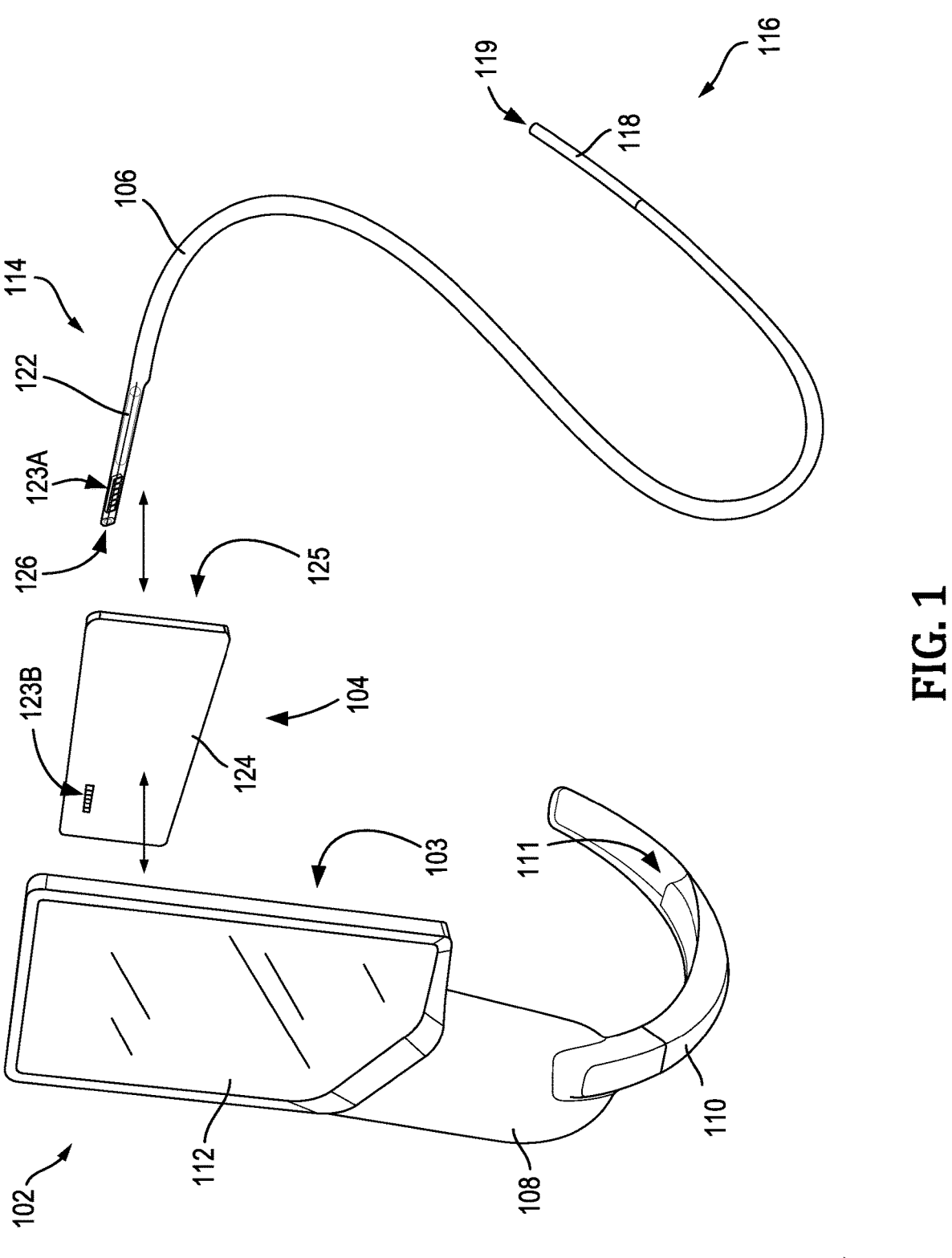
FIG. 1 depicts an example video system that includes a steerable endoscope.

Patients who require breathing assistance may be connected to a mechanical ventilator via breathing tube (e.g., an endotracheal tube). In a medical procedure referred to as an intubation, a clinician inserts a breathing tube into the mouth of the patient, past the larynx, and into the trachea. The breathing tube may then be connected to a ventilator or other device for supplying breathing gases to the patient. A laryngoscope may be used during intubation to help the clinician manipulate portions of the patient's anatomy, such as the tongue and epiglottis, and obtain a view of the larynx sufficient for inserting the breathing tube into the trachea. To further help visualize the larynx, some laryngoscopes may be configured with a video camera. A laryngoscope that includes a video camera may be referred to as a video laryngoscope (VL).

With some patients, performing an intubation may be difficult due to a variety of factors, such as inability to position the head or neck of the patient (e.g., due to injury), airway obstruction, atypical anatomy of the patient, other health considerations, or a combination of these or other factors. In these types of scenarios, clinicians may augment the use of a VL with a steerable endoscope, which is a narrow, flexible tube that typically includes its own video camera system integrated into a steerable distal tip that is inserted into the patient's body. The proximal end of the endoscope is removably connected to an external device capable of displaying video images from the endoscope camera and receiving control input from the user for controlling the steerable tip. In some examples, the endoscope may be connected to a VL designed to receive the endoscope and function both as a VL and as a display/control device for the endoscope.

During intubation, the endoscope may be navigated into the airway and positioned such that it provides supplemental visualization of the airway and facilitates insertion of the breathing tube. In some examples, the breathing tube is passed over the endoscope and into position in the airway, with the endoscope itself serving as a channel or guide for inserting the breathing tube. An endoscope used as a guide for breathing tube insertion may perform the same or similar functions as an introducer and may alternatively be referred to as an introducer in some examples.

The endoscope may include an internal channel that passes from the proximal end (where the channel is accessible to the clinician during intubation) to the distal tip of the endoscope (where the channel opens to the airway). This channel, which may be referred to as a working channel, provides additional functionality to the endoscope that may further facilitate intubation. For example, an intubation may be performed on a conscious patient, such as during awake tracheal intubation (ATI). During ATI, a clinician may use the working channel to apply a topicalizing agent (e.g., lidocaine or other local anesthetic) to portions of the airway to reduce patient discomfort and anxiety, and to improve patient tolerance of the breathing tub. In other examples (such as in non-airway applications), the working channel may be used for passing small instruments, such as tissue sampling instruments, catheters, or other types of instruments. In still other examples, the working channel may be used to apply suction during operation of the endoscope.

In addition to the working channel, elements associated with control of the endoscope steerable tip may also be routed between the proximal and distal ends. In one example, the proximal end of the endoscope may include a drive system that controls the steerable tip via one or more pairs of pull wires, which are routed along the outside of the working channel and are connected to interior portions of the steerable tip. Each pair of pull wires may be connected to the drive system such that the pull wires of each pair work in opposition to one another to cause articulation of the steerable tip in a movement plane. For instance, the pull wires of a pull wire pair may connect to opposite sides of the steerable tip for causing articulation in a first movement plane (e.g., a left/right movement plane). The drive system may increase tension on a first pull wire and decrease tension on a second (opposing) pull wire to cause articulation in a first direction (e.g., left). Similarly, releasing tension on the first pull wire and increasing tension on the second pull wire causes articulation of the steerable tip in a second direction (e.g., right). The endoscope may include a second pair of pull wires arranged to cause articulation of the steerable tip in a second movement plane (e.g., an up/down movement plane).

The present disclosure describes systems and methods for manufacturing a steerable endoscope with a steerable distal tip. An example manufacturing method includes using a single extrusion to fabricate the internal structure of the endoscope, where the working channel forms the center of the structure, and a set of auxiliary channels surround the working channel. The auxiliary channels are used to route the pull wires that articulate the steerable tip and the electrical conductors associated with the operation of the camera system and other electrical elements located in the steerable tip. The manufacturing method may improve the efficiency of the manufacturability and assembly of the endoscope by enabling reductive or subtractive manufacturing processes. For example, the flexibility of the extrusion may be modified in one or more regions (such as in the region that forms the steerable tip) by removing material from the outer portions of the extrusion. Further, outer portions of the extrusion may be cut or sliced to simplify the insertion of pull wires and electrical conductors into the auxiliary channels. Additional details are now provided by way of discussion of the drawings.

FIG. 1 depicts an example medical video system 100 that includes a video laryngoscope (VL) 102 capable of connecting to, and providing steering control of, a steerable endoscope 106, through a detachable cartridge 104. The endoscope distal end 116 includes a steerable tip 118 and accessories 119, which may be used during operation of the endoscope 106. For example, the accessories 119 may include a camera system (e.g., a video camera, lights, etc.) that captures image data (e.g., video images of the airway) during use. The accessories 119 may also include sensors, such as an accelerometer or inertial measurement unit (IMU), which provides measurement data associated with the acceleration, angular velocity, position, and/or other variables associated with the position/orientation/movement of the steerable tip 118. In some examples, the accessories 119 may further include one or more instrument ports, such as a port for a working channel and one or more auxiliary channels, as described herein.

The steerable tip 118 is connected to a drive system 122 by one or more pairs of pull wires (depicted in FIGS. 4A-B), which are routed along the length of the endoscope 106. At the endoscope distal end 116 the pull wires are terminated at different points on the interior of the steerable tip 118 and/or at other points on the interior of the distal end 116. At the endoscope proximal end 114, the pull wires connect to elements of the drive system 122. The drive system 122 may include mechanical and/or electro-mechanical elements, such as one or more electric motors, drums, gears, and/or other elements suitable for applying steering forces to the pull wires. As described above, elements of the drive system 122 cause the wires of each pull wire pair to work in opposition to each other to cause articulation of the endoscope steerable tip 118 within a movement plane.

The endoscope proximal end 114 also includes an electrical interface 123A, through which the endoscope 106 may receive electrical power and may transmit/receive signals to/from the VL 102. For example, the electrical interface 123A provides power and/or steering control signals from the VL 102 to the drive system 122 for controlling the movement of the endoscope steerable tip 118. The electrical interface 123A also provides a source of input power for operating the accessories 119 (such as the camera system, sensors, etc.), and/or other sensors or electronic elements included within the endoscope 106.

Further, the electrical interface 123A provides a data path for transmitting sensor data, video images, and/or other types of data from the endoscope 106 to the VL 102. For instance, video image data captured by the endoscope camera system may be transmitted to the VL 102 via the electrical interface 123A. In some examples, signals or data (such as clock, enable, timing, and/or other signals) may be transmitted/received through the electrical interface 123A in order to enable or configure operation of the endoscope 106.

The electrical interface 123A may include a plurality of electrical contacts, such as conductive pads, receptacles, pins, balls, ports, and/or other type of electrical contacts that are connected to elements of the endoscope 106 by a plurality of conductors routed within the interior of the endoscope 106. The conductors (depicted in FIGS. 4A-B) may include one or more wires, flexible printed circuits (FPCs), and/or other types of electrical conductors suitable for distributing power and establishing signal connection between the electrical interface 123A and elements of the endoscope 106.

In addition, the endoscope 106 may include an access port 126 that provides access to the working channel and to one or more auxiliary channels of the endoscope 106. As described above, in some examples, a topical agent may be delivered to the airway during intubation through the working channel, via the access port 126. For instance, a syringe, catheter, or other type of medical device may be inserted through the access port 126 and into the working channel for delivery of the topicalizing agent, which is dispensed into the airway at an exit port provided with the accessories 119. In other examples, the access port 126 and working channel may be used for other purposes, such as the application of suction, the insertion of tissue-sampling instruments, and/or for another purpose.

In the example video system 100, the access port 126 is located at the proximal tip of the endoscope 106, where the working channel may be routed around or through the drive system 122 and electrical interface 123A. In other examples, the access port 126 may be located elsewhere in or near the endoscope proximal end 114. For instance, the access port 126 may be located distally from the drive system 122.

To connect the endoscope 106 to the VL 102, the endoscope proximal end 114 is connected to the detachable cartridge 104, which serves as an electrical and/or mechanical interface between the VL 102 and endoscope 106. In other examples, the endoscope 106 may connect to the VL

102 by another type of cartridge 104, or the endoscope 106 may connect directly to the VL 102, such as at a connection port included with the VL 102.

The endoscope 106 may be connected to the cartridge 104 by any of a variety of methods. In one example, the endoscope 106 may slide into receiving elements on the cartridge front surface 125 that retain the endoscope 106 to the cartridge 104. In other examples, the steerable endoscope 106 may connect to the cartridge 104 by another method. When the endoscope proximal end 114 is connected to the cartridge 104, the electrical interface 123A is conductively connected to a corresponding electrical interface on the cartridge front surface 125 (not depicted). The cartridge 104 further includes an electrical interface 123B on the cartridge rear surface 124, for making electrical connection with the VL 102. Within the cartridge 104, the electrical interface 123B is connected to the electrical interface on the cartridge front surface 125, such as by wiring, pins, printed circuit board (PCB), flex, and/or other type of electrical connection.

The cartridge 104 may be connected and retained to the VL rear surface 103 by any of a variety of methods, such as by permanent magnets located within the VL 102 and/or cartridge 104, or by other elements that apply force between the VL 102 and cartridge 104. When the cartridge 104 is connected to the VL 102, the electrical interface 123B is conductively connected to a corresponding electrical interface on the VL rear surface 103 (not depicted). The VL 102 provides electrical power to the endoscope 106 through the described electrical connections of the cartridge 104, and signals may be transmitted/received between the VL 102, cartridge 104, and endoscope 106.

In examples where the endoscope drive system 122 includes electric motors for articulating the steerable tip 118, the VL provides power and control signals to the motors via the electrical interface 123A-B. In other examples, the drive system 122 may include passive mechanical elements (such as drums, gears, etc.) that couple to mechanical elements of the cartridge 104 and receive steering forces generated in the VL 102 or cartridge 104. In such an example, the endoscope 106, cartridge 104, and/or VL 102 may include a mechanical interface for transmitting these steering forces from motors in the VL 102 or cartridge 104 to the passive mechanical elements of the drive system 122.

The VL 102 includes a display 112, a handle 108, and a blade or extension 110, which includes a camera 111 positioned at the distal end of the blade or extension 110. The VL 102 may include additional functions or features typically associated with a video laryngoscope, such as a power source (e.g., a battery), processor, memory, and other electronic components.

In an example, the VL 102 receives data (such as video images and sensor data) from the steerable endoscope 106 through the cartridge 104 and displays the received data on the display 112. The display may be capable of displaying images from multiple cameras simultaneously, such as images from the VL camera 111 and the endoscope camera, such as by split screen, picture-in-picture, or other display methods. The display 112 may be any of a variety of display technologies, such as LCD, LED, OLED, or other display technology. In examples, the display 112 may be a touch-sensitive display (e.g., a capacitive touch-sensitive display) that allows the user to provide steering input through the display 112. Elements of the VL 102 may translate the steering inputs to corresponding motor outputs for articulating the endoscope steerable tip 118.

Additionally, or alternatively, the endoscope 106 may be connected to other types of external devices capable of receiving the endoscope proximal end and establishing mechanical and/or electrical connection with the endoscope 106. In examples, the external device may provide steering control of the endoscope steerable tip 118 and may receive image data from the endoscope 106.

Figure 2A:
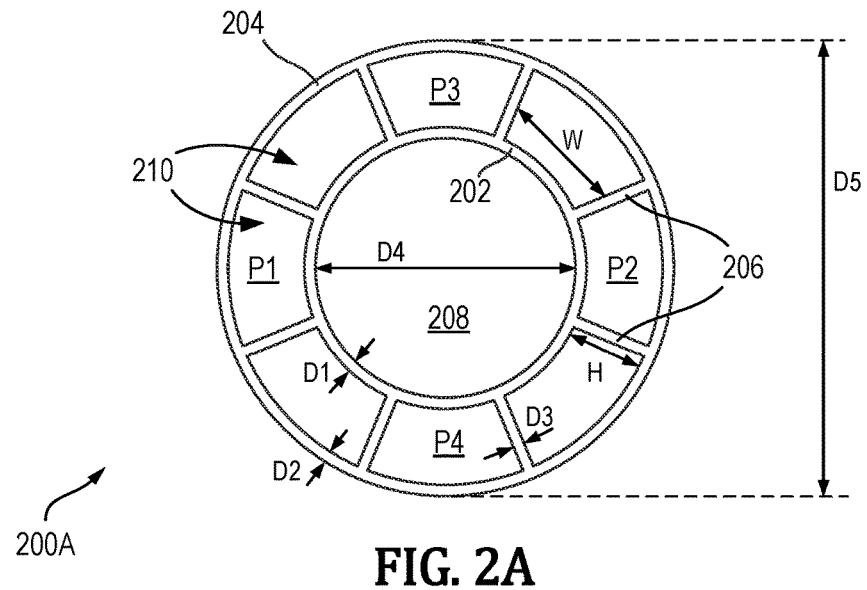
FIG. 2A depicts an example cross-section used to form an extrusion.
Figure 2B:
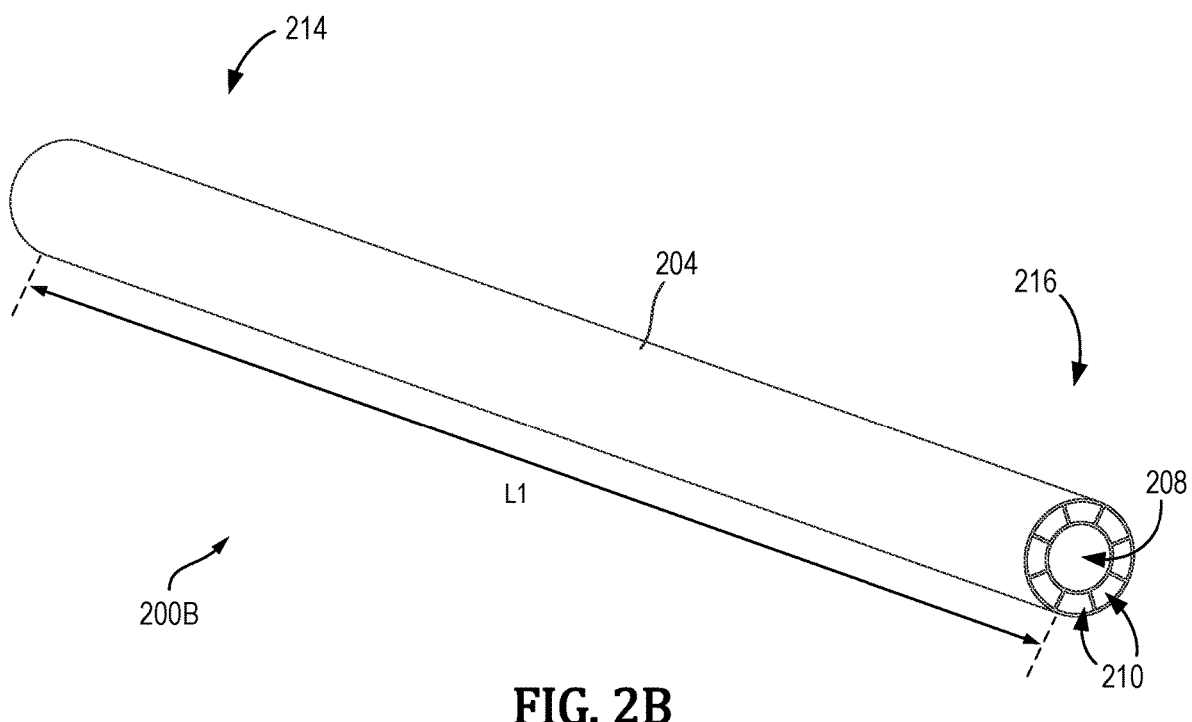
FIG. 2B depicts an example extrusion of the example cross-section.

FIG. 2A depicts an example cross-section 200A that forms the structure of an endoscope, and FIG. 2B depicts an example extrusion 200B of the example cross-section 200A, from which an endoscope (such as endoscope 106) may be fabricated. The example cross-section 200A includes an inner wall 202 and an outer wall 204, connected by a plurality of fins 206. The inner wall 202 may be substantially cylindrical, and the inner wall 202 defines an inner lumen, which may be considered a working channel 208. The outer wall 204 may also be substantially cylindrical and a second lumen is formed between the inner wall 202 and the outer wall 204. The fins 206 partition the space or lumen between the inner wall 202 and outer wall 204 into a plurality of auxiliary channels 210. The fins 206 may run the length of the extrusion 200B. The fins 206 may be protrusions of material that extend from the outer surface of the inner wall 202 to the inner surface of the outer wall 204.

As described above, the working channel 208 may be used during operation of the endoscope to administer topicalizing agent, perform suction, insert instruments (such as tissue sampling instruments), and/or to perform other functions associated with the use of the endoscope. The auxiliary channels 210 may be used to perform similar functions as the working channel 208, such as for providing a topicalizing agent, suction, or for some other purpose topicalizing agent. The auxiliary channels 210 may also carry mechanical actuation components, such as pull wires, and electrical components, such as electrical wires, through the length of the endoscope.

The flexibility of the extrusion 200B (and the endoscope fabricated therefrom) depends on a number of parameters associated with the design of the example cross-section 200A. For example, the thickness D1 of the inner wall 202, thickness D2 of the outer wall 204, and thickness D3 of the fins 206 each contribute to the overall flexibility of the example extrusion 200B. To achieve a desired flexibility, D1, D2, and D3 may be independently selected. For instance, an example cross-section 200A with a greater D1, D2, and/or D3 may result in an example extrusion 200B that is less flexible, and an example cross-section 200A with a lesser D1, D2, and/or D3 may result in an example extrusion 200B that is more flexible.

Further, the flexibility of the extrusion 200B is affected by the number of fins 206 included in the example cross-section 200A, where a greater number of fins 206 result in an example extrusion 200B that may be less flexible, and a fewer number of fins 206 result in an example extrusion 200B that may be more flexible. The number and spacing of the fins 206 also affects the number and size of the auxiliary channels 210. In examples where the fins 206 are uniformly spaced from one another, such as in example cross-section 200A, a greater number of fins 206 decreases the distance W between the fins 206, and a fewer number of fins 206 increases the distance W between the fins 206. Thus, the number of fins 206 affects the space available within each auxiliary channel 210 for routing pull wires and/or electrical conductors (depicted in FIGS. 4A-B). In some examples, the number of fins 206 may be between 4-10 fins or 6-8 fins.

In some examples, the fins 206 may not be uniformly spaced from one another. For example, the fins 206 may be grouped into a plurality of sets that each include two or more fins 206, where the distance between fins 206 within each set is smaller than the distance between sets. As one example, fins 206 may be grouped into sets that each include three fins 206 that are closely spaced. The distance between fins 206 within each set may form auxiliary channels 210 that may or may not be sufficiently sized for routing pull wires or conductors, or for performing other functions associated with the endoscope. However, the sets of fins 206 may be sufficiently separated from one another to form larger auxiliary channels 210 that can accommodate pull wires, conductors, etc.

The number and spacing of the fins 206 included in the example cross-section 200A may be chosen based on the number and type of elements routed in the auxiliary channels 210, and the desired position of the elements around the circumference of the example cross-section 200A. For instance, example cross-section 200A includes eight fins 206 that partition the space between the inner wall 202 and outer wall 204 into eight auxiliary channels 210. Because the fins 206 are evenly spaced around the circumference of the example cross-section 200A, the eight auxiliary channels 210 are spaced at 45° intervals around the example cross-section 200A. This arrangement permits opposing pull wires of a first pull wire pair to each be routed within auxiliary channels 210 positioned on opposite sides of the cross-section (180° apart) from each other. For example, a first pull wire of a first pull wire pair may be routed in an auxiliary channel 210 located at position P1, and a second (opposing) pull wire of the first pull wire pair may be routed in an auxiliary channel located at position P2. A second pull wire pair may be similarly routed in a second pair of auxiliary channels 210 that are oriented perpendicular from the first pair. For example, the pull wires of the second pull wire pair may be routed in auxiliary channels 210 located at positions P3 and P4. In other examples, the pull wire pairs may be routed in other auxiliary channels 210 according to the movement plane in which the pull wire pairs articulate the endoscope steerable tip.

In addition, the fins 206 may not all have the same thickness D3 as one another. In some examples, select fins 206 may be designed with greater or lesser thickness D3 than other fins 206. A fin 206 with a greater thickness D3 may be more rigid than a fin 206 with a lesser thickness D3. Further, in FIG. 2A, the example cross-section 200A depicts fins 206 with uniform thickness D3 along the entire height H. However, the thickness D3 of each of the fins 206 may be varied along the height H to control the overall flexibility of the example extrusion 200B. For instance, one or more fins 206 may be tapered, such that a fin 206 may be designed wider (e.g., greater D3) near the inner wall 202 and narrower (e.g., lesser D3) near the outer wall 204. In other examples, the profile of thickness D3 along the height H of each fin 206 may be selected to achieve a desired flexibility of the example extrusion 200B.

The height H of the fins 206 may also be selected to control flexibility of the extrusion 200B. For example, increasing H may increase the flexibility of the extrusion 200B, and decreasing H may decrease the flexibility of the example extrusion 200B. In some examples, the diameter D4 of the inner wall 202 may also be selected in conjunction with H, in order to achieve a desired diameter D5, which affects the finished diameter of the endoscope.

The flexibility of the example extrusion 200B may also be controlled by selection of the material comprising the example cross-section 200A. For instance, a material with a higher durometer results in an example extrusion 200B that is less flexible, and a material with a lower durometer results in an example extrusion 200B that is more flexible. In some examples, a material with a durometer in the range of 35D-50D may provide the example extrusion 200B with suitable flexibility. In one example, the example cross-section 200A and example extrusion 200B may be fabricated with an elastomer such as PEBAX®, or with a material with similar elastomeric properties.

As described, the example cross-section 200A is extruded from a single material to form the example extrusion 200B. In some examples, during fabrication, the example cross-section 200A may be extruded to length L1 (depicted in FIG. 2B), which may be a substantial proportion of the finished length of the endoscope. In other examples, the example cross-section 200A may be extruded to lengths greater than L1 then cut to length L1 to form a substantial portion of the finished length of the endoscope. Once extruded or cut to length L1, one end of the extrusion 200B may be treated as a distal end 216 and the other end treated as a proximal end 214 for additional fabrication steps.

Figure 3:
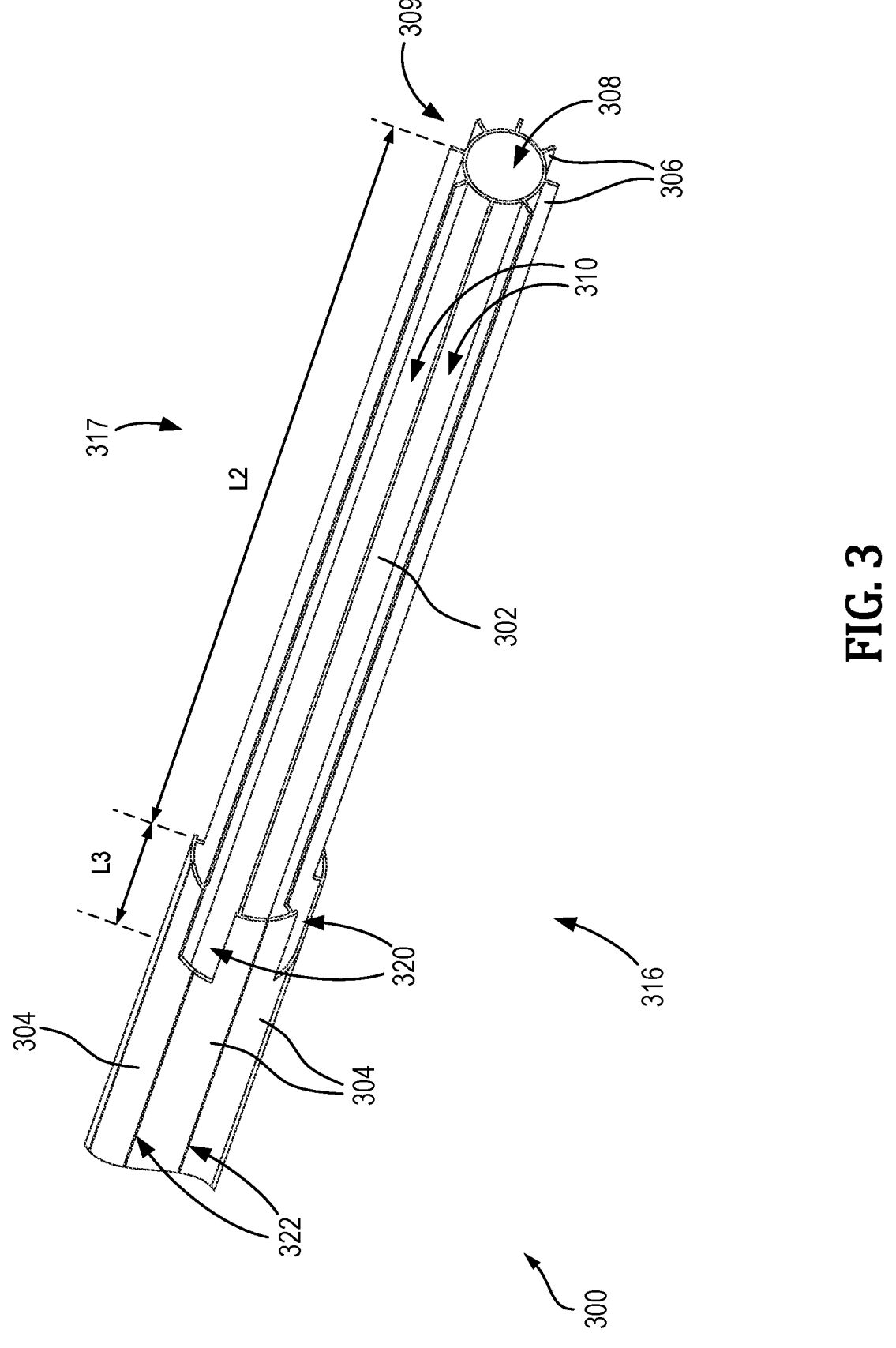
FIG. 3 depicts a view of the distal end of an example extrusion.

FIG. 3 depicts an enhanced view of the distal end 316 of an example extrusion 300, which may be similar to, or the same as, example extrusion 200B that has been further modified during fabrication. Example extrusion 300 may be based on example cross-section 200A.

At the distal end 316 of example extrusion 300, a length L2 of the outer wall 304 is removed to form a bendable region 317, which extends proximally from the distal tip 309 of the example extrusion 300. In some examples, the length L2 may be between about 20-80 mm, 30-70 mm, 35-50 mm, 50-150 mm, 75-100 mm. A shorter length of L2 may be advantageous for increased deflection given a linear pull range. A longer length of L2 may be advantageous for visualization at the shallowest angle possible and may improve the tip's ability to guide the rest of the endoscope. The removal of the outer wall 304 from the bendable region 317 increases the flexibility of the example extrusion 300 in the bendable region 317, relative to portions of the example extrusion 300 where the outer wall 304 is not removed, which may be referred to as the main body portion of the endoscope. The main body portion of the endoscope may extend at least 80-90% of the length of the endoscope. For instance, the outer wall 304 may extend at least 70-90% of the endoscope length. The inner wall 302 extends further than the outer wall 304. For instance, the inner wall 302 may extend at least 80%, 90%, or 95% of the of the length of the endoscope. As described below with respect to FIGS. 4A and 6A, the bendable region 317 may be further modified to form a steerable tip (such as steerable tip 118).

In some examples, the removal of the outer wall 304 in the bendable region 317 may result in the removal of a portion of the material from the fins 306 in the same region. For instance, the height of the fins 306 in the bendable region 317 may be reduced from original height H (depicted in FIG. 2A). The reduced height the of fins 306 is sufficient for defining auxiliary channels 310 in the bendable region 317. In other examples, removal of the outer wall 304 in the bendable region 317 may not affect the height of the fins 306, which may remain at the original height H. The inner wall 302 and working channel 308 may remain unaffected by the removal of the outer wall 304 in the bendable region 317.

In some examples, additional portions of the outer wall 304 may be removed over a length L3 of the example extrusion 300 to form access windows 320. The access windows 320 are adjacent to the proximal end of the bendable region 317 and are formed above auxiliary channels 310 in which pull wires may be routed (depicted in FIGS. 4A-B). In addition, slots 322 may be cut through the outer wall 304, down the full length of the example extrusion 300. The slots 322 allow pull wires, electrical conductors, and/or other elements of the endoscope to be inserted into the auxiliary channels 310. For instance, the pull wires may be pushed through the slots 322 along the length of the endoscope instead of having to thread the pull wire through a fully closed auxiliary channel 310. In examples where one or more of the auxiliary channels 310 is used to provide a topicalizing agent, suction, or for some other purpose, slots 322 may not be cut in the corresponding auxiliary channels 310.

In some examples, additional outer wall material may be removed from regions of the proximal end of the example extrusion 300. For instance, additional windows, which may be similar to, or the same as, access windows 320, may be formed at the proximal end of the example extrusion 300, above auxiliary channels 310 in which pull wires may be routed. In some examples, the length of the additional windows may be a longer or shorter than the length L3 of windows 320.

Figures 4A, 4B:
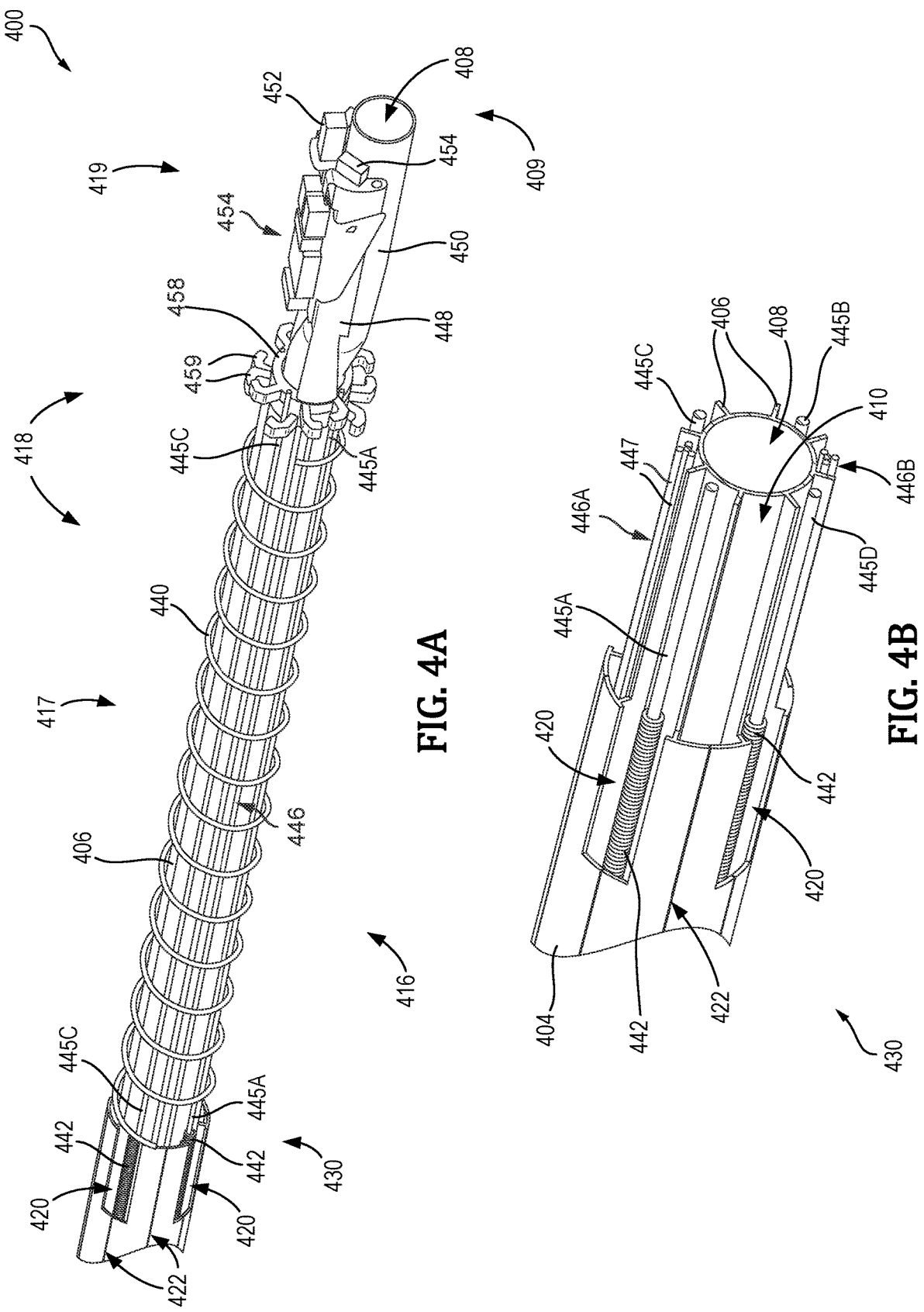
FIGS. 4A-4B depict views of the distal end of a modified example extrusion.

FIG. 4A depicts an enhanced view of the distal end 416 of an example extrusion 400, where elements have been added to the example extrusion 400 to form a steerable tip 418. FIG. 4B depicts an enhanced view of a region 430 near the windows 420 of example extrusion 400, where region 430 has been rotated clockwise to improve visibility. The example extrusion 400 may be similar to, or the same as, example extrusion 300 depicted in FIG. 3. For instance, the example extrusion 400 includes an outer wall 404, fins 406, a working channel 408, auxiliary channels 410, windows 420, and other elements that may be similar to, or the same as, corresponding elements of example extrusion 300.

Example extrusion 400 further includes two pairs of pull wires 445A-D, which may be more easily visualized in FIG. 4B. The pull wires 445A-D may be arranged so that a first pair of pull wires 445A-B are routed on opposite sides of the working channel 408. A second pair of pull wires 445C-D are also arranged on opposite sides of the working channel 408, but the second pair of pull wires 445C-D are oriented 90° from the first pull wires pair 445A-B as shown. This arrangement allows the first pull wire pair 445A-B to cause articulation of the steerable tip 418 in a first movement plane (e.g., a left/right movement plane) and the second pull wire pair 445C-D to cause articulation of the steerable tip 418 in a second movement plane (e.g., an up/down movement plane) that is orthogonal to the first movement plane. In other examples, the pull wires 445A-D may be arranged to control articulation of the steerable tip 418 in other movement planes.

As described above, the pull wires 445A-D may be routed down the length of the example extrusion 400 and connected to a drive system (such as drive system 122) located at the proximal end. The drive system includes elements that control tension on the pull wires 445A-D. During operation of the endoscope, flexion of the endoscope along its length may affect the amount of tension on the pull wires 445A-D, which may cause unwanted articulation of the steerable tip 418. To reduce the potential for unwanted articulation, each of the pull wires 445A-D may be routed inside a separate lumen 442, which may be a coiled pipe or similar structure. The separate lumens 442 may be coiled springs that present low contact friction to the pull wires 445A-D. Flexion of the endoscope may cause the separate lumens to slide freely over the pull wires 445A-D without transmitting additional tension to the pull wires 445A-D, and/or significantly affecting articulation of the steerable tip 418.

The separate lumens 442 may be coiled metal wire or other material suitable for providing low contact friction for the pull wires 445A-D. In some examples, rather than coiled springs, the separate lumens 442 may be another type of structure suitable that reduces friction and/or is substantially incompressible during endoscope flexion. For instance, the coil pipe maintains its same length between its two ends regardless of how much the endoscope body is bent or manipulated during operation. During fabrication of the endoscope, the pull wires 445A-D may be combined with the separate lumens 442, such as by wrapping the metal wire of the separate lumens 442 around each pull wire 445A-D. Each pull wire/separate lumen assembly may be pressed or rolled through the slots 422, until separate lumens 442 and pull wires 445A-D are routed along the full length of each auxiliary channels 410, from the proximal end to the steerable tip 418. The separate lumens 442 and pull wires 445A-D are routed in auxiliary channels 410 where material from the outer wall 404 has been removed to form the windows 420. Once positioned in the appropriate auxiliary channel 410, adhesive may be applied through the windows 420 to affix the separate lumens 442 to the example extrusion 400. In some examples, the separate lumens 442 may be similarly affixed to the example extrusion 400 at the extrusion proximal end, such as by application of adhesive through windows located in the proximal end.

Similarly, a first set of electrical conductors 446A and second set of electrical conductors 446B are pressed or rolled through slots 422 into remaining (unused) auxiliary channels 410. The electrical conductors 446A-B may include an arrangement of one or more individual conductive elements 447, such as one or more electrical wires, FPCs, and/or other type of flexible conductive elements. In some examples, conductive elements 447 may be grouped into greater or fewer sets of electrical conductors 446A-B, and/or may be routed in greater or fewer auxiliary channels 410. The electrical conductors 446A-B provide power and signal connections between electrical elements located in proximal portions of the endoscope (such as electrical interface 123A) and electrical elements located in the steerable tip 418.

The bendable region 417 may also include a spring 440. In examples that include the spring 440, the electrical conductors 446A-B and pull wires 445A-D are routed within auxiliary channels 410 through the bendable region 417 under the spring 440. The spring 440 is described in further detail below with respect to FIG. 6A. The electrical conductors 446A-B and pull wires 445A-D terminate within the accessory region 419 of the steerable tip 418.

The accessory region 419 may include a guide tube 450 connected to the distal tip (such as distal tip 309) of the example extrusion 400. The guide tube 450 may be affixed to the example extrusion 400 by any suitable method, such as by adhesive, thermal bonding, or other method of fixation. The guide tube 450 extends and introduces a bend in the working channel 408, in order to create space for electrical elements associated with features and functions of the endoscope (such as accessories 119). The electrical elements may include a camera 452 and light source 454 (e.g., an LED or the like), and may include additional active and/or passive circuit components 456. The circuit components 456 may include sensors, such as an accelerometer, IMU, and/or other types of sensors, and may include other types of electrical components.

The camera 452, light source 454, and circuit components 456 may be mounted to a common PCB, FPC, or other type of circuit board, or in some examples may be mounted to two or more separate circuit boards that are electrically connected. The circuit board(s) may be secured to a mounting scaffold 448, which may contact portions of the guide tube 450 and/or portions of the example extrusion 400. The mounting scaffold 448 may be affixed to the guide tube 450 and/or portions of the example extrusion 400, such as by adhesive or other method. In some examples, the guide tube 450 may be substantially straight or may be shaped or bent in a number of possible configurations. The mounting scaffold 448 may be designed to accommodate the camera 452, light source 454, and circuit components 456 accordingly.

Figure 5A:
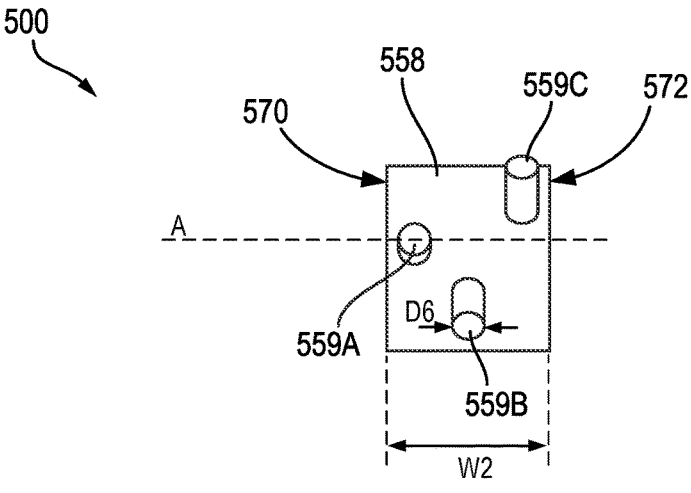
FIGS. 5A-5C depict an example method for securing pull wires to a mounting ring.
Figure 5B:
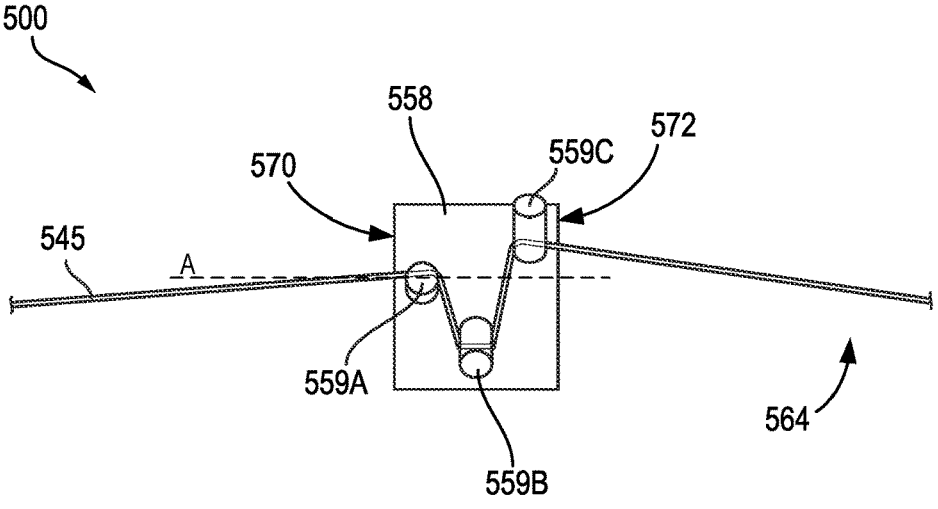

The mounting scaffold 448 may also be connected to a mounting ring 458, which may be affixed to portions of the guide tube 450 and/or example extrusion 400. The mounting ring 458 includes a plurality of posts 459 that are used to affix the ends of pull wires 445A-D to the mounting ring 458. An example method for securing the ends of the pull wires 445A-D to the mounting ring 458 via posts 459 is depicted in FIG. 5A-B and described below. The mounting scaffold 448 and mounting ring 458 may be a single continuous element, or in some examples, may be separate elements.

The mounting scaffold 448 and mounting ring 458 may include wire routes (not depicted) that provide for the passage of electrical conductors 446A-B from the auxiliary channels 410 to the circuit board(s) associated with the camera 452, light source 454, and/or circuit components 456. The conductive elements 447 of electrical conductors 446A-B may connect to the circuit board(s) by any of a number of known methods for establishing electrical connection, such as by soldered connection, pluggable connector, and/or other forms of electrical connection. Accordingly, the electrical conductors 446A-B are electrically coupled to the sensors or other electrical components of the endoscope, such as the camera.

Additionally, as described above, one or more of the auxiliary channels 410 (e.g., auxiliary channels 410 not used for routing pull wires 445A-D or electrical conductors 446A-B) may be used to perform functions that require direct access to the airway. For example, one or more auxiliary channels 410 may be used to deliver topicalizing agent, apply suction, or for another purpose. In such examples, one or more of the auxiliary channels 410 may also be routed through the accessory region 419, to the distal tip 409.

Figure 5C:
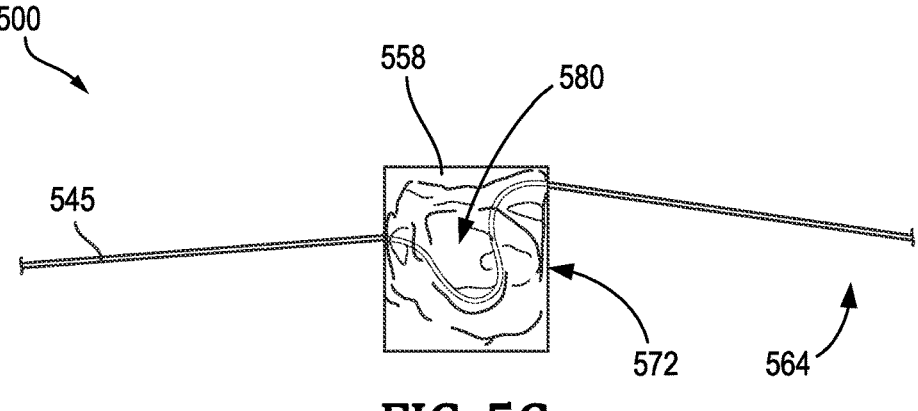

FIGS. 5A, 5B, and 5C depict an example system 500 for affixing a pull wire 545 to a mounting ring 558. More specifically, FIGS. 5A-C depict a side view of the mounting ring at progressive stages of the manufacturing process. The pull wire 545 and mounting ring 558 may be similar to, or the same as, pull wires 445A-D and mounting ring 458, respectively, which are depicted in FIGS. 4A-B. For example, the mounting ring 558 may be annular, and may be mounted to portions of an extrusion (such as example extrusion 400) or a guide tube (such as guide tube 450). Although example system 500 is shown for a single pull wire 545, additional pull wires may be similarly affixed to the mounting ring 558 as described below.

The mounting ring 558 includes a set of three posts 559A-C, which are arranged on the mounting ring 558 as depicted in FIG. 5A. In the example depicted, the first post 559A is located nearest the proximal side 570 of the mounting ring 558 and is positioned along reference line A, where the first post 559A may intersect the pull wire 545 routed in an auxiliary channel (such as one of the auxiliary channels 410). In examples, the reference line A may represent the approximate route of the pull wire 545 on the proximal side 570 of the mounting ring 558, as illustrated in FIG. 5B. The second post 559B may be located vertically below reference line A and is positioned horizontally between the first post 559A and third post 559C. The third post 559C may be located nearest the distal side 572 of the mounting ring 558, vertically above reference line A.

The posts 559A-C may be formed from a material that has a particular melting point that is lower that than of the materials surrounding the posts 559A-C. For instance, the posts 559A-C may melt at a lower temperature than the other elements of endoscope proximate the posts 559A-C. The material of the posts 559A-C may be a plastic, thermoplastic, or other type of thermally sensitive material. At elevated temperatures, such as at temperatures sufficiently above normal body temperature (37° Celsius), the posts 545A-C may soften and/or become pliable. In some examples, at elevated temperature, the posts 545A-C may enter a liquid or semiliquid state, where the posts 545A-C may deform or melt. The process of applying heat to a material previously formed into a shape or element (such as a post 559A-C) to intentionally cause the material to deform or melt into a new shape or element may be referred to as thermal reflow or reflow. When heat is removed from the material following reflow, the material cools and solidifies to maintain the new shape.

In some examples, the posts 559A-C and mounting ring 558 may be the same type of thermally sensitive material and formed in the same molding or extrusion process, while in other examples the posts 559A-C and mounting ring 558 may be made of different types of materials. The posts 559A-C may be affixed to the mounting ring 558 using adhesive or by another method of fixation. In examples, the posts 559A-C may be part of the mounting ring 558 or may be extensions of the mounting ring 558. For instance, the posts 559A-C and mounting ring 558 may be formed as a single element, such as a single molded part. In further examples, the posts 559A-C and mounting ring 558 may be continuous with, or part of, other structures or elements of the endoscope, (e.g., mounting scaffold 448).

In the example depicted in FIG. 5B, the pull wire 545 is routed clockwise around the first post 559A to the second post 559B, counterclockwise around the second post 559B to the third post 559C, and clockwise around the third post 559C. Following the final bend at the third post 559C, the pull wire 545 is routed away from the distal side 572 of the mounting ring 558. In some examples, tension may be maintained on the distal end 564 of the pull wire 545, such as by an external element (not depicted).

With the pull wire 545 routed around the posts 559A-C, heat is applied to the posts 559A-C to cause the material of the posts 559A-C to reflow and cover or engulf the portions of the pulls wires 55 surrounding the posts 559A-C. As depicted in FIG. 5C, when the heat is removed, the reflowed material of the posts 559A-C solidifies to form a reflow region 580 that is continuous with the mounting ring 558 and that secures the pull wire 545 within the reflow region 580 and to the mounting ring 558. In some examples, the posts 559A-C may reflow into two or more reflow regions 580 that secure two or more portions of the pull wire 545 within the reflow regions 580 and to the mounting ring 558. Following reflow, the distal end 564 of the pull wire 545 may be severed and discarded. For example, the distal end of the pull wire 545 may be cut at, or near, the distal side 572 of the mounting ring 558.

The arrangement of posts 559A-C and routing of the pull wire 545 around the posts 559A-C is designed to increase adhesion of the pull wire 545 to mounting ring 558 when the posts 559A-C are reflowed. For example, the arrangement of the posts 559A-C results in the pull wire 545 following a route through the reflow region 580 that is approximately S-shaped, which increases the surface area of the pull wire 545 in contact with the mounting ring 558 and reflow region 580. In addition, the S-shaped route of the pull wire 545 distributes the forces applied to the pull wire 545 through the reflow region 580 during articulation of the endoscope steerable tip. A broader distribution of the forces within the reflow region 580 may reduce instances where the pull wire 545 becomes loose or breaks free from the mounting ring 558 when tension is applied to the pull wire 545.

In some examples, the posts 559A-C may be designed to further increase contact between the pull wire 545 and the mounting ring 558 and reflow region 580, and to further distribute steering forces (i.e., tension) applied to the pull wire 545 to the mounting ring 558 and reflow region 580. For example, the posts 559A-C may be designed with a larger diameter D6 (depicted in FIG. 5A), so that the route of the pull wire 545 around the posts 559A-C is increased. A longer route around the posts 559A-C results in more surface area of the pull wire 545 being in contact with the reflow region 580 when the posts 559A-C are reflowed and may increase the distribution of steering forces from the pull wire 545 to the reflow region 580 and mounting ring 558.

Additionally, or alternatively, the mounting ring 558 may be designed with an increased or decreased width W2. In examples where the width W2 of the mounting ring 558 is increased, the posts 559A-C may be spread farther apart horizontally, which may increase the length of the pull wire route within the reflow region 580 but may cause the S-shaped route around the posts 559A-C to be less pronounced or more shallow. As a result, steering forces applied to the pull wire 545 may not be as broadly distributed to the reflow region 580 following reflow. In examples where the width W2 of the mounting ring 558 is decreased, the posts 559A-C may be spaced closer together horizontally, which decreases the length of the pull wire route within the reflow region 580 but may cause the S-shaped route around the posts 559A-C to be more pronounced. As a result, steering forces applied to the pull wire 545 may be more broadly distributed to the reflow region 580 and mounting ring 558 following reflow.

Additionally, or alternatively, the posts 559B-C may be vertically spaced farther from reference line A, which may increase the length of the route of the pull wire 545 through the reflow region 580 and may help distribute steering forces from the pull wire 545 to the reflow region 580 and mounting ring 558. In some examples, the posts 559A-C may include features that facilitate connection between the pull wire 545 and the reflow region 580 and mounting ring 558. For instance, as depicted in FIG. 4A, the posts 559A-C may include hooks or portions of hooks that may further ensure contact between the pull wire 545 and reflow region 580 when the posts 559A-C are reflowed. In other examples, the posts 559A-C may include other features, or may be shaped and/or arranged in a manner that facilitate fixation of the pull wire 545 to the posts 559A-C, reflow region 580, and/or mounting ring 558.

Figures 6A, 6B:
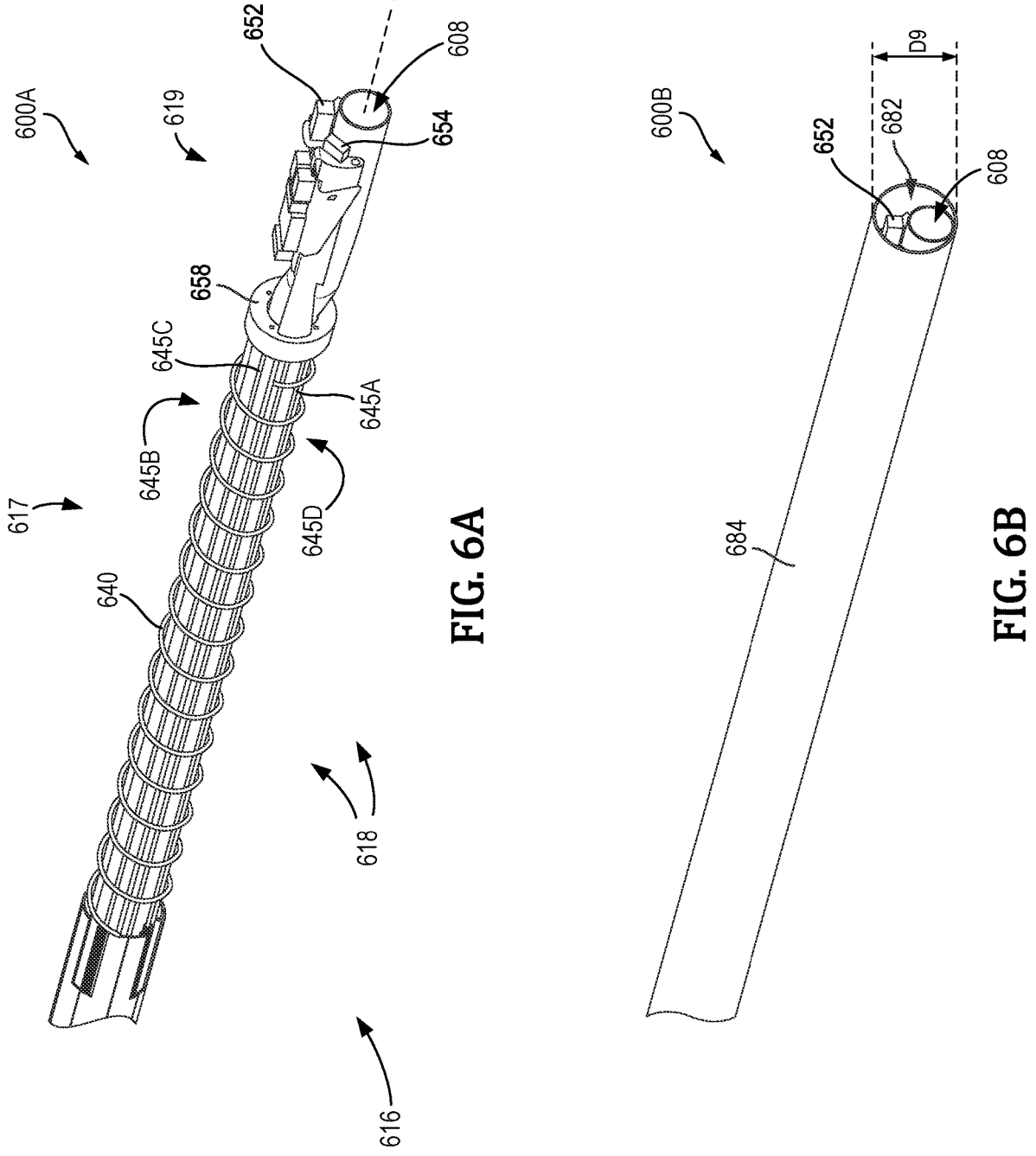
FIGS. 6A-6B depict views of the steerable tip of an example endoscope.

FIG. 6A depicts the distal end 616 of an example endoscope 600A with pull wires 645A-D affixed to the mounting ring 658. The example endoscope 600A may be similar to, or the same as, example extrusion 400, and may include the same or similar elements depicted above in FIGS. 4A-B. For instance, example endoscope 600A includes four pull wires 645A-D, which may be similar to, or the same as, pull wires 445A-D. In FIG. 6A, pull wires 645A, C are visible, and pull wires 645B, D are routed on the opposite side of the example endoscope 600A and are not visible.

The pull wires 645A-D are affixed to the mounting ring 658 by the reflow process described above for mounting ring 558. Briefly, each pull wire 645A-D is routed around a set of dedicated posts (such as posts 449 or 559A-C) and held in relatively equal tension (such as by external elements that are not depicted). At the proximal end of the example endoscope 600A (depicted in FIG. 1), the pull wires 645A-D are affixed to elements of the endoscope drive system (such as drive system 122), which may remain static during the reflow process. Heat is applied to the reflow the material of the posts and then the heat is removed, allowing the material to cool and solidify, and securing each pull wire 645A-D to the mounting ring 658. As described above, the distal ends of the pull wires 645A-D may be severed near the mounting ring 658 and removed.

The example endoscope 600A also includes a bendable region 617 and an accessory region 619, which together form a steerable tip 618. With the pull wires 645A-D held in relatively equal tension during reflow, the steerable tip 618 is maintained in a neutral or non-articulated orientation. In the neutral orientation (depicted in FIG. 6A), the bendable region 617 is substantially straight along its entire length and may be substantially parallel to axis C of the working channel 608 in the accessory region 619. The spring 640 helps maintain the neutral position of steerable tip 618.

FIG. 6B depicts an example endoscope 600B, where an outer jacket 684 has been added to example endoscope 600A. The outer jacket 684 is a thin-walled tube that seals the example endoscope 600 while allowing articulation of the steerable tip 618, and flexion along the length of the example endoscope 600B. Accordingly, the outer jacket 684 may be fabricated using a material with a high degree of flexibility, such as a thin polyurethane extrusion, or other type flexible material. In some examples, the outer jacket 684 may be designed to achieve a low durometer, such as a durometer in the range of 30 a-40 a. In other examples, the outer jacket 684 may be fabricated from materials that exhibit a lower or higher durometer range.

The thickness of the outer jacket 684 may be substantially less than 1 mm, such that the outer jacket 684 minimally increases the outer diameter of the underlying extrusion. For instance, the outer diameter D9 of the example endoscope 600B may be minimally larger than the outer wall diameter D5 (e.g., less than 5% larger), depicted in FIG. 2A for the example cross-section 200A. In some examples, the outer diameter D9 of the example endoscope 600B may be approximately 5 mm, while in other examples the outer diameter D9 of the example endoscope 600B may be more or less than 5 mm.

A transparent or semi-transparent sealant may be applied to a portion of the aperture 682, in the space between the working channel 608 and outer jacket 684, leaving the distal end of the working channel 608 open to the patient's airway. The sealant protects the electrical elements of the accessory region 619 while allowing light generated by the light source 654 to illuminate the patient's airway and the camera 652 to capture images of the airway. In examples where one or more of the auxiliary channels (such as auxiliary channels 410) are used to administer topicalizing agent, suction, or to perform another function within the patient's airway, the auxiliary channels may be routed through the accessory region 619 and terminate at the aperture 682. Sealant may also be applied around the auxiliary channel(s) while leaving the distal end(s) the auxiliary channel(s) open to the airway.

As described above for pull wires 445A-D, pull wires 645A-B may form a first pull wire pair, where tension may be applied to pull wire 645A and released from pull wire 645B to cause articulation in a first direction (e.g., left), and vice versa for articulation in a second direction (e.g., right). Pull wires 645C-D may form a second pull wire pair that may function the same as the first pull wire pair 645A-B, but cause articulation in another movement plane (e.g., up/down).

With the pull wires 645A-D affixed to the mounting ring 658, tension applied to one of pull wires 645A-D (and released from the corresponding opposing pull wire 645A-D) is transmitted to the mounting ring 658, which causes flexion of the bendable region 617 and spring 640. The accessory region 619 is therefore articulated in the direction of the applied tension.

In addition to helping maintain the bendable region in a neutral position during attachment of the pull wires 645A-D, the spring 640 may also provide for smooth articulation of the steerable tip 618 during operation of the example endoscope 600B. For instance, the spring 640 may apply restoring force to the steerable tip 618 in the direction of the neutral position, which may reduce regions in the movement range where steering control may be less responsive.

In some examples, rather than a spring 640, the bendable region 617 may include another type of element or elements capable of applying force to the bendable region 617 and accessory region 619. For example, the bendable region 617 may include a tubular structure with elastic properties, capable of flexing during articulation and applying restoring force to the steerable tip 618.

FIG. 7 depicts an example method 700 for fabricating a steerable endoscope. At operation 702, a cross-section (such as example cross-section 200A) is extruded to form the underlying structure of a steerable endoscope (such as endoscope 106). The cross-section may include the features discussed above. For instance, the cross-section may be substantially circular, and includes an inner wall (e.g., inner wall 202) connected to a larger diameter outer wall (e.g., outer wall 204) by a plurality of radially directed fins (e.g., fins 206). The fins partition the space between the inner and outer walls into a plurality of auxiliary channels (e.g., auxiliary channels 210), which may be used for routing pull wires (e.g., pull wires 445A-D), electrical conductors (e.g., electrical conductors 446A-B), or for other purposes as described above.

The cross-section may be extruded using known extrusion techniques. For example, the cross-section may be extruded using a single-screw or twin-screw extruder that forces material through a die, which shapes the material in the form of the described cross-section. In some examples, the extrusion process may include applying heat to the material to soften and/or combine it or may include using another process to soften and/or combine the material to form the extrusion.

At operation 704, the extrusion is cut to a desired length (e.g., a length L1). In some examples, the extrusion may be cut to length during the extrusion process, such as by a cutting element associated with the extruder. The length of the cut extrusion may be a substantial portion of the length of the finished endoscope. For instance, the length of the cut extrusion may be more than 80-90% of the length of the finished endoscope (e.g., including guide tube and drive system).

At operation 706, the outer wall is removed from a portion (such as a length L2) of the distal end of the cut extrusion to form a bendable region (e.g., bendable regions 317 and 417), where removal of the outer wall increases the flexibility of the extrusion in the bendable region. In some examples, the outer wall may be removed from more than a 1-2 cm or 1-5 cm portion of the distal end of the extrusion. In some examples, removal of the outer wall may cause removal of a portion of the fins in the bendable region, while in other examples the fins may be substantially unaffected by removal of the outer wall.

At operation 708, an additional portion (such as a length L3) of the outer wall is removed from the distal end of the cut extrusion to form windows (e.g., windows 320) above each auxiliary channel in which a pull wire will be routed (described below for operation 712). The windows are formed adjacent to the proximal end of the bendable region. Additional windows may be formed at the proximal end of the cut extrusion, above the same auxiliary channels in which the pull wires will be routed. In some examples, windows may be formed above other auxiliary channels in which pull wires are not routed. In other examples, no windows may be formed at the distal end of the cut extrusion.

At operation 710, slots (e.g., slots 322 and 422) are cut down the length of the cut extrusion, from the distal end to the proximal end, and above each of the auxiliary channels. Where windows are present, the slots are cut from the opening of each window to the proximal end. Where windows are not present, the slots are cut from the bendable region to the proximal end. The slots may be cut using any of a wide variety of cutting methods suitable for cutting the material of the extrusion. In examples where one or more of the auxiliary channels is used to provide a topicalizing agent, suction, or for some other purpose, slots may not be cut in the corresponding auxiliary channels.

At operation 712, for auxiliary channels designated for routing pull wires, separate lumens 442 with pull wires installed are inserted through the slots and into the appropriate auxiliary channels. During insertion, the separate lumens and/or pull wires may be pressed through the slots by any of a variety of methods suitable for doing so. The pull wires may be installed in the separate lumens prior to operation 712. For example, the separate lumens may be formed or wrapped around the pull wires in a process performed prior to assembly of the endoscope.

With the separate lumens and pull wires inserted into the auxiliary channels, adhesive may be applied through the windows formed at operation 712 to affix the distal ends of the separate lumens within their respective auxiliary channels. In examples, the proximal ends of the separate lumens may also be secured within their respective auxiliary channels using adhesive or other method securing the separate lumens. As described above, with one or both ends of each separate lumen (e.g., coil pipe) secured within the auxiliary channels, flexion of the endoscope causes flexion of the separate lumens without significantly affecting the tension on the pull wires.

Additionally, for auxiliary channels designated for routing electrical conductors (e.g., electrical conductors 446A-B), the electrical conductors are also pressed through the slots and into the appropriate auxiliary channels. As described above, the electrical conductors may include one or more wires, FPCs, and/or other types of electrically conductive elements. The electrical conductors may be pressed through the slots and inserted into the auxiliary channels by any of a variety of methods suitable for doing so, such as by the same or similar method used to insert the separate lumens and pull wires.

At operation 714, a guide tube (e.g., guide tube 450) is connected to the distal end of the cut extrusion. The guide tube introduces a bend in the working channel to accommodate a camera system (e.g., camera 452, light source 454, etc.) and other elements around the working channel at the endoscope distal tip. The guide tube may be affixed to the distal end of the extrusion by any of a variety of methods, such as by adhesive, thermal bonding methods, or other methods. The guide tube and associated elements may function as an accessory region (e.g., accessory region 419). Together, the bendable region and the accessory region may function as a steerable tip (e.g., steerable tip 118 and 618).

At operation 716, a spring (e.g., spring 440 and 640) is installed over the bendable region at the distal end of the cut extrusion. The spring helps maintain the bendable region in the neutral (unbent) position while pull wires are secured at the endoscope distal end, such as described above with respect to FIGS. 5A-C and 6A. The spring also applies a restoring force to help return the steerable tip toward the neutral position during articulation, when tension is released from one or more of the pull wires. In some examples, the function of the spring may be performed by another element capable of applying force toward the neutral position when the bendable region is articulated away from neutral. For example, a thin-walled elastic tube or other type of elastic element may be used in lieu of a spring.

At operation 718, the pull wires may be connected to a mounting ring (e.g., mounting ring 458, 558, or 658) or similar element suitable for affixing one or more pull wires. As described above, each pull wire may be routed around one or more posts associated with the mounting ring, and heat applied to reflow the posts. The reflowed material of the posts is then allowed to cool and solidify to secure the pull wires. The pull wires may be cut or trimmed to remove excess pull wire length that extends distally from the reflow region. In other examples, other methods may be used to secure the pull wires to the mounting ring or other element(s) of the steerable tip. For example, the pull wires may be secured by adhesive, welding, or by other fixation method.

In some examples, prior to connecting the distal end of the pull wires to the mounting ring, the proximal end of the pull wires may be connected to elements of the endoscope drive system (e.g., drive system 122). The drive system may statically hold the proximal end of the pull wires so that tension may be applied to the pull wires during the reflow process.

In addition, the electrical conductors are connected to circuit elements located in the accessory region. For example, wires may be soldered to pads, posts, or other types of connection elements. In examples where the electrical conductors include one or more FPCs, connection between each FPC and corresponding circuit element(s) may be made by mating connectors. In other examples, the electrical conductors may be connected to circuit elements by any of a variety of established methods for making electrical connections. At the endoscope proximal end, the electrical conductors may be connected to elements of the electrical interface (e.g., electrical interface 123A).

At operation 720, an outer jacket (e.g., outer jacket 684) is installed over the assembly to complete the endoscope fabrication. The outer jacket is a thin-walled tube that seals the endoscope, while allowing the endoscope to remain flexible, and the steerable tip to be articulated. Accordingly, the outer jacket may be made of a material with a high degree of flexibility, such as a thin polyurethane extrusion, or other type of material that may be made thin and flexible.

At the endoscope distal tip, the end of the outer jacket forms an aperture (e.g., aperture 682) that coincides with the end of the working channel. The space between the outer jacket and the working channel may be at least partially filled with a transparent or semi-transparent sealant to protect elements of the accessory region, while allowing the endoscope camera system to illuminate and image the airway through the sealant.

Prior to installing the jacket, an opening may be made in the outer jacket at the proximal end to allow the outer jacket to be fit around the electrical interface. The outer jacket may be further sealed around the electrical interface and proximal tip of the endoscope, such as with an adhesive, sealant, or the like.

Those skilled in the art will recognize that the methods and systems of the present disclosure may be implemented in many manners and as such are not to be limited by the foregoing aspects and examples. In other words, functional elements being performed by a single or multiple components. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A method for manufacturing an endoscope, the method comprising:
   extruding a cross-section to form an extrusion, the extrusion comprising:
      an inner wall defining a first lumen;
      an outer wall defining a second lumen between the inner wall and the outer wall; and
      a plurality of fins extending from the inner wall to the outer wall and defining a plurality of auxiliary channels in the second lumen;
   removing the outer wall from a portion of a distal end of the extrusion to form a bendable region;
   cutting slots in the outer wall above at least two of the auxiliary channels;

inserting a pull wire through one of the slots and into one of the auxiliary channels; and
installing an outer jacket covering the extrusion including the bendable region.

2. The method of claim 1, further comprising cutting the extrusion to a length of the endoscope.

3. The method of claim 1, further comprising installing a spring over the auxiliary channels of the bendable region.

4. The method of claim 1, further comprising inserting electrical conductors through the slots and into the auxiliary channels.

5. The method of claim 1, further comprising:
   routing a distal end of the pull wire around posts protruding from a mounting ring; and
   thermally reflowing the posts to secure the pull wire to the mounting ring.

6. The method of claim 1, wherein the plurality fins include at least 4 fins.

7. An endoscope comprising:
   an outer jacket extending a length of the endoscope;
   an outer wall, interior to the outer jacket, of an extrusion extending at least 80% of the length of the endoscope and ending at a bendable region of the endoscope;
   an inner wall, interior to the outer wall, extending at least 90% of a length of the endoscope and through the bendable region, the inner wall defining a working channel through the endoscope;
   a plurality of fins extending from the inner wall to the outer wall and defining a plurality of auxiliary channels between the inner wall and the outer wall;
   a first pull wire extending through a first auxiliary channel of the plurality of auxiliary channels; and
   a second pull wire extending through a second auxiliary channel of the plurality of auxiliary channels.

8. The endoscope of claim 7, wherein the first auxiliary channel is positioned opposite the working channel from the second auxiliary channel.

9. The endoscope of claim 8, further comprising:
   a third pull wire extending through a third auxiliary channel of the plurality of auxiliary channels; and
   a fourth pull wire extending through a fourth auxiliary channel of the plurality of auxiliary channels, wherein the fourth auxiliary channel is positioned opposite the working channel from the third auxiliary channel.

10. The endoscope of claim 7, wherein an access window is cut in the outer wall, above the first auxiliary channel, adjacent and proximal to the bendable region.

11. The endoscope of claim 7, wherein the first pull wire is positioned within a first separate lumen and the second pull wire is positioned with a second separate lumen.

12. The endoscope of claim 7, further comprising:
   a camera positioned at a distal end of the endoscope; and
   an electrical conductor electrically coupled to the camera and extending through a third auxiliary channel of the plurality of auxiliary channels.

13. The endoscope of claim 7, further comprising a spring wrapped around the bendable region and positioned interior to the outer jacket.

14. The endoscope of claim 7, wherein the plurality of fins include at least 6 fins.

15. The endoscope of claim 7, further comprising a guide tube, at a distal end of the endoscope, supporting one or more sensors.

* * * * *